US012672894B2

(12) United States Patent
Decker

(10) Patent No.: US 12,672,894 B2
(45) Date of Patent: Jul. 7, 2026

(54) PERFORATION GUARD

(71) Applicant: KONINKLIJKE PHILIPS N.V., Eindhoven (NL)

(72) Inventor: Cedar Decker, Albertville, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 18/265,992

(22) PCT Filed: Dec. 14, 2021

(86) PCT No.: PCT/EP2021/085757
§ 371 (c)(1),
(2) Date: Jun. 8, 2023

(87) PCT Pub. No.: WO2022/129090
PCT Pub. Date: Jun. 23, 2022

(65) Prior Publication Data
US 2024/0090917 A1 Mar. 21, 2024

Related U.S. Application Data

(60) Provisional application No. 63/126,032, filed on Dec. 16, 2020.

(51) Int. Cl.
*A61B 17/3207* (2006.01)
*A61B 18/24* (2006.01)
*A61B 90/00* (2016.01)

(52) U.S. Cl.
CPC .... *A61B 17/320758* (2013.01); *A61B 18/245* (2013.01); *A61B 90/08* (2016.02); *A61B 2090/08021* (2016.02)

(58) Field of Classification Search
CPC ........ A61B 17/3207; A61B 17/320758; A61B 17/320725; A61B 17/32075; A61B 17/320783
See application file for complete search history.

(56) References Cited

U.S. PATENT DOCUMENTS 4,772,258 A * 9/1988 Marangoni .... A61B 17/320758
606/159
2003/0055444 A1 3/2003 Evans
(Continued)

FOREIGN PATENT DOCUMENTS

WO 2012009675 A2 1/2012

OTHER PUBLICATIONS

Left Anterior Descending Coronary Artery Wall Thickness Measured by High-Frequency Transthoracic and Epicardial Echocardiography. Irmina Gradus-Pizlo, Brian Bigelow, Yousuf Madhomed, Stephen Sawada, Karen Rieger, Harbey Feingenbaum. The American Journal of Cardiology vol. 91 Jan. 1, 2003 (Year: 2003).*

(Continued)

*Primary Examiner* — Tuan V Nguyen

(57) ABSTRACT

A thrombectomy or atherectomy device (10) includes a thrombectomy or atherectomy catheter (12) including a cutter (20), and a physical barrier (22, 24) disposed proximate to the cutter. In some examples, the physical barrier (22, 24) can have a stiffness effective for the physical barrier to deflect a blood vessel having a thickness less than a first predetermined thickness threshold and effective for a thrombus or atheroma on an inner wall of the blood vessel to deflect the physical barrier.

16 Claims, 7 Drawing Sheets

(56)                    References Cited

U.S. PATENT DOCUMENTS

| | | | |
|---|---|---|---|
| 2005/0137622 A1* | 6/2005 | Griffin ............. | A61B 17/12136 |
| | | | 606/198 |
| 2007/0112370 A1* | 5/2007 | Andrews ............. | A61M 25/104 |
| | | | 604/103.09 |
| 2007/0208370 A1 | 9/2007 | Hauser | |
| 2009/0099581 A1 | 4/2009 | Kim | |
| 2012/0197193 A1* | 8/2012 | Krolik .................. | A61B 5/6853 |
| | | | 604/99.04 |
| 2012/0239064 A1 | 9/2012 | Cartier | |
| 2017/0143359 A1* | 5/2017 | Nguyen ......... | A61B 17/320758 |
| 2019/0060613 A1 | 2/2019 | Sharman | |
| 2020/0178992 A1 | 6/2020 | Wallace | |

OTHER PUBLICATIONS

International Search Report and Written Opinion Dated Apr. 5, 2022 for International Application No. PCT/EP2021/085757 Filed Dec. 14, 2021.

* cited by examiner

10

12

16

20

18

14

22

10

14

16

20

18

24

12

26

100

Compact physical barrier into catheter   ⟵ 102

Insert catheter into blood vessel   ⟵ 104

Deploy physical barrier adjacent a cutter   ⟵ 106

Cut thrombus or atheroma with cutter   ⟵ 108

Control cutting with physical barrier   ⟵ 110

PERFORATION GUARD

CROSS REFERENCE TO RELATED APPLICATIONS

This application is the U.S. National Phase application under 35 U.S.C. § 371 of International Application No. PCT/EP2021/085757 filed Dec. 14, 2021, which claims the benefit of U.S. Provisional Patent Application No. 63/126, 032 filed Dec. 16, 2020. These applications are hereby incorporated by reference herein.

FIELD

The following relates generally to the catheter arts, thrombectomy arts, atherectomy arts, and related arts.

BACKGROUND

Thrombectomy and atherectomy devices are medical devices designed to remove tissue or material from inside a diseased vessel (e.g., an artery, a vein, etc.). Intravascular devices attempt to remove this material without surgically opening the vessel. The mechanisms of intravascular removal can include simple suction, mechanical cutting, chemical dissolution, ablation through heat or light, maceration by mechanical or sonic energy, and so forth. As the material in the diseased vessel matures, it requires more aggressive mechanisms to disrupt and remove it. These mechanisms often come with the added risk of difficulty in distinguishing between the diseased material and the vessel wall, thus leading to unintended vessel wall damage and potentially vessel wall perforations.

The following discloses certain improvements to overcome these problems and others.

SUMMARY

In some embodiments disclosed herein, a thrombectomy or atherectomy device includes a thrombectomy or atherectomy catheter including a cutter, and a physical barrier disposed proximate to the cutter.

In some embodiments disclosed herein, a thrombectomy or atherectomy device includes a thrombectomy or atherectomy catheter including a cutter, and a cage disposed proximate to the cutter. The cage has a stiffness effective for the physical barrier to deflect a blood vessel having a thickness less than a first predetermined thickness threshold and effective for a thrombus or atheroma on an inner wall of the blood vessel to deflect the cage.

In some embodiments disclosed herein, a thrombectomy or atherectomy method includes: inserting a catheter carrying a cutter into a blood vessel to deliver the cutter to a thrombus or atheroma disposed on an inner wall of the blood vessel; cutting the thrombus or atheroma using the cutter to remove at least a portion of the thrombus or atheroma; and controlling the cutting using a physical barrier disposed proximate to the cutter in which the physical barrier the deflected when cutting the thrombus or atheroma to allow the cutter to engage the thrombus or atheroma and the physical barrier deflecting the wall of the blood vessel to prevent the cutter from engaging the wall of the blood vessel.

One advantage resides in providing an intravascular device with a safeguard feature to prevent blood vessel perforations.

Another advantage resides in providing an intravascular device with a physical barrier to deflect healthy blood vessel walls during a thrombectomy or atherectomy procedure.

Another advantage resides in providing an intravascular device with a physical barrier to surround a cutting device during a thrombectomy or atherectomy procedure.

Another advantage resides in providing an intravascular device with a physical barrier comprising a flexible cage to deflect healthy blood vessel walls during a thrombectomy or atherectomy procedure.

Another advantage resides in providing an intravascular device with a physical barrier comprising an inflatable balloon structure to deflect healthy blood vessel walls during a thrombectomy or atherectomy procedure.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
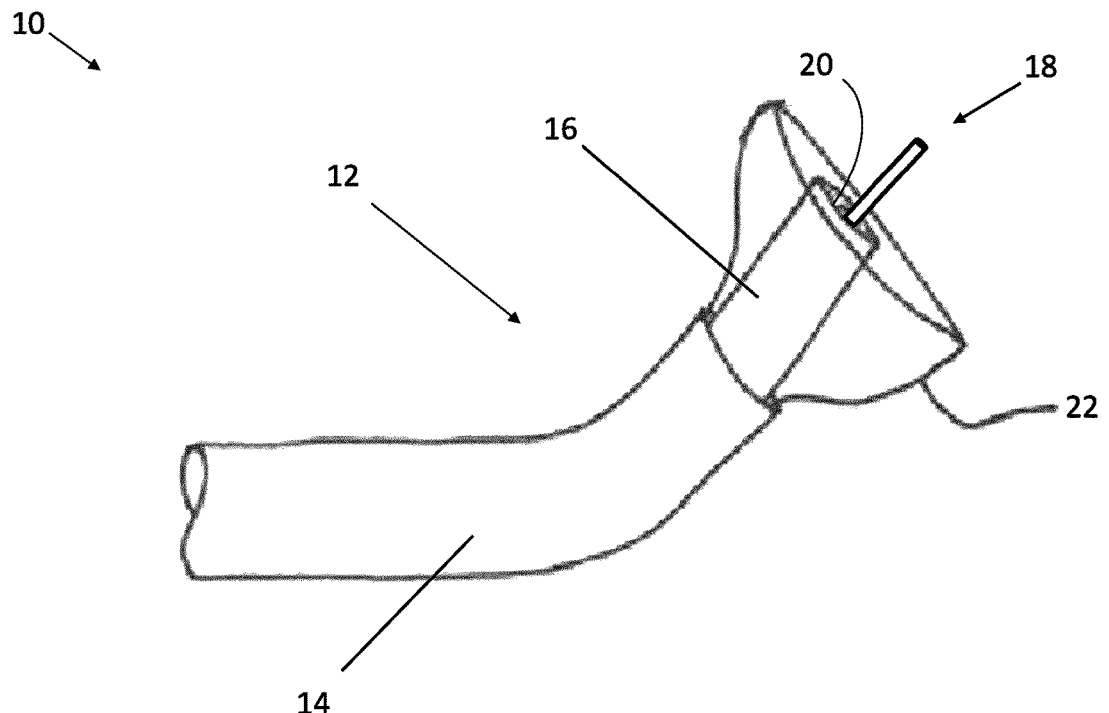
FIG. 1 diagrammatically illustrates a thrombectomy or atherectomy device in accordance with the present disclosure.

The following relates to an improved thrombectomy or atherectomy device. Such devices are used to remove atherosclerosis (i.e., plaque buildup) in an artery (atherectomy procedure) or to remove a thrombus or collagen buildup in a vein (thrombectomy procedure). These procedures are typically performed in the peripheral vascular system to treat blood vessels in a leg or arm, although the procedures may be applied to treat blood vessels in other anatomical areas.

In such a procedure, a thrombectomy or atherectomy device is delivered by catheterization, typically along a guide wire, to the location of the buildup. The thrombectomy or atherectomy device includes a cutter, such as (but not limited to) a rotating drum cutter, an abrasion cutter, or a laser cutter. The rotating drum or abrasion cutter operates by direct contact with the buildup, while a laser cutter typically has about a 50-micron working distance. Hence, the catheter carrying the device has a fixed bend or is steerable/deflectable to bring the catheter tip bearing the cutter into proximity or contact with the buildup to be removed.

A concern with a thrombectomy or atherectomy procedure is the potential to cut into the healthy vessel wall, thereby producing a weakened (or potentially even ruptured) vessel wall. The procedure is typically done as image-guided therapy (iGT) under X-ray imaging guidance; however, this imaging does not provide a highly detailed image of the vessel wall, and typically X-ray-absorbing marker(s) are disposed on the thrombectomy or atherectomy device to assist in visualizing the location of the device in the body.

The devices and methods disclosed herein is premised on the observation that the healthy blood vessel wall is typically thin, e.g., 0.4 mm thick in some peripheral blood vessels, and hence is pliable. By contrast, the blood vessel wall on which the thrombus or atherosclerosis is formed is usually much thicker, e.g., several millimeters thick, and hence much less pliable.

Recognizing this, in some embodiments disclosed herein, a cage or other physical barrier is disposed proximate to (e.g., around) the catheter tip that bears the cutter. The cage has a stiffness profile that allows it to retain its shape and push away a thin, pliable healthy blood vessel wall. However, the cage is sufficiently pliable that it deflects when pressed against a diseased vessel wall that is less pliable due to thickening caused by thrombus or atherosclerosis. Hence, the cage deflection allows the cutter to engage the diseased vessel wall to cut away the thrombus or atherosclerosis, but the cage prevents the cutter from cutting into a thin and pliable healthy vessel wall.

In some non-limiting embodiments disclosed herein, the outer diameter of the cage surrounding the cutter is about 1 mm larger than the diameter of the cutter (or of the inner sheath of the catheter bearing the cutter). This ensures that the cage, when not deflected, will keep the cutter at least 0.5 mm away from the deflected healthy vessel wall. (For comparison, the catheter inner sheath typically has a diameter of about 2.5 mm, while a vascular stent has a typical expanded diameter of 10 mm or larger). The cage has sufficient stiffness to push away a healthy vessel wall while being sufficiently pliable to deflect when the catheter tip is pressed against a stiff diseased vessel wall with the level of force used in the thrombectomy or atherectomy procedure. Notably, arteries typically have thicker walls than veins, so the cage stiffness is typically designed to be higher for an atherectomy device as compared with a thrombectomy device.

In some embodiments disclosed herein, the cage is a braided Nitinol structure. Nitinol is a metal alloy of nickel and titanium in which the Ni and Ti are present in roughly equal atomic percentages. Nitinol advantageously can be shaped and then heat set at typically 350 400° C., and the heat-set nitinol braided structure is compressible to facilitate compaction inside an outer sheath of the delivery catheter. Instead of a braided nitinol cage, a laser-cut nitinol cage could also be used. The stiffness of the cage is suitably designed by optimizing parameters such as the braid density (a higher braid density, e.g., as measured in PPI or pitch angle, provides a stiffer cage), wire diameter of the Nitinol wires (larger wire diameter increases cage stiffness), or so forth. Wires of other materials such as cobalt-chromium (CoCr) or stainless steel (SST) are also contemplated for constructing the braided cage. In a variant illustrative embodiment, the cage is not braided but rather comprises closed nitinol wire loops arranged around the cutter, is constructed using laser cutting of a preformed Nitinol cage, or so forth.

Delivery of the thrombectomy or atherectomy device with the cage deployed could be problematic as the cage could interfere with movement of the device through the vessel. Accordingly, in some embodiments disclosed herein, the delivery catheter includes an inner sheath that carries the cutter, and an outer sheath that is coaxial with and surrounds the inner sheath. The cage is initially drawn back into the outer sheath to compact the cage for delivery. When the device reaches the site of the buildup to be removed, the cage is deployed, e.g., by pulling back the outer sheath or pushing the cage outside of the outer sheath. This deployment can use mechanical mechanisms similar to those used in deployment of a stent, except that one end of the cage remains attached to the catheter by a retaining ring or other suitable attachment. After the procedure is complete, the cage is drawn back and compacted into the outer sheath for the catheter removal process.

In other embodiments disclosed herein, the cage could be replaced by an annular balloon disposed around the tip of the delivery catheter. The balloon would be deflated during delivery and then inflated to form an annular balloon disposed around the cutter that has a diameter that is larger than that of the cutter (or carrying inner sheath) by a suitable amount such as about 1.0 mm in some non-limiting embodiments; and the inflated balloon has a stiffness profile effective to push away a thin healthy blood vessel but deform when pressed against a stiffer diseased and thickened blood vessel. The stiffness of the balloon can be designed by the optimizing the wall thickness of the bag forming the balloon, the stiffness of the material making up the bag, and by optimizing the inflation pressure.

With reference to FIG. 1, an illustrative thrombectomy or atherectomy device 10 is shown. As shown in FIG. 1, the device 10 includes a thrombectomy or atherectomy catheter 12. The catheter 12 includes one or more sheaths. For example, the illustrative catheter 12 includes an outer sheath 14 that is coaxial with and surrounds an inner sheath 16. The device 10 is optionally inserted along a guide wire 18 that extends through the inner sheath 16 (or in some cases, if the inner sheath 16 is omitted, then the guide wire 18 can extend through the outer sheath 14). In this approach, the guide wire 18 is first inserted into the blood vessel under X-ray imaging guidance, and then the catheter 12 is inserted along the guide wire 18. A cutter 20 is disposed on a portion of the catheter 12. As shown in FIG. 1, the cutter 20 is disposed at an end of the catheter 12; although the cutter can be disposed on any portion of the catheter. For example, the cutter 20 can be disposed on the inner sheath 16. The cutter 20 is configured to cut, abrase, ablate, ultrasonically disintegrate, or otherwise remove (i.e., cut) a blood clot (e.g., a thrombus), plaque (e.g., atheroma), or other undesired material disposed on a blood vessel wall. By way of non-limiting illustrative example, the cutter 20 can comprise a rotating cutter, an abrasion cutter, a laser cutter, or any other suitable cutter.

FIG. 1 also shows a physical barrier 22 disposed proximate to the cutter 20. As shown in FIG. 1, the physical barrier 22 can comprise a cage surrounding the cutter 20. The cage has a diameter that is larger than the diameter of the cutter 20 and/or larger than the diameter of the inner sheath 16 carrying the cutter. In some non-limiting illustrative embodiments, the cage has a diameter that is at least 0.9 millimeters larger than a diameter of the cutter 20. In another embodiment, the physical barrier 22 may not surround the cutter 20 but rather may only be disposed proximate to the cutter 20 (see FIG. 4). In another embodiment, the physical barrier 22 is suitably a balloon that, when inflated, is disposed proximate to the cutter 20. In some examples, the balloon can comprise an annular balloon that surrounds the cutter 20 when inflated.

Figure 2:
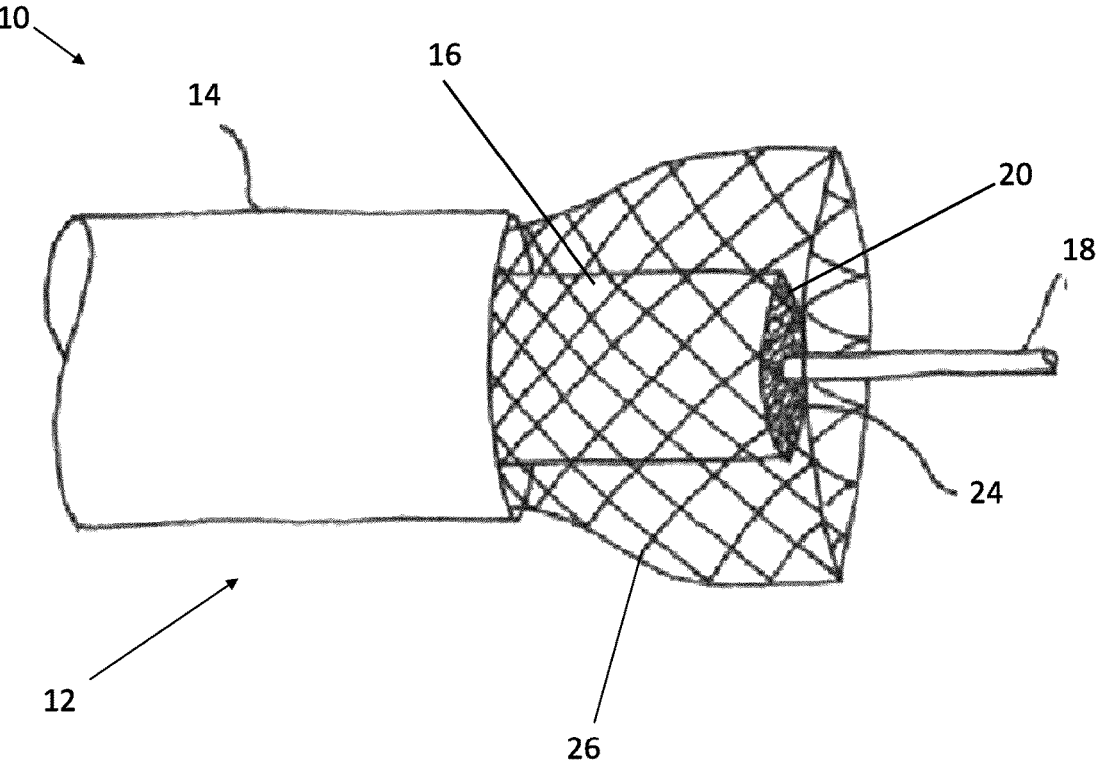
FIGS. 2-4 diagrammatically illustrate other embodiments of the device of FIG. 1.
Figure 3:
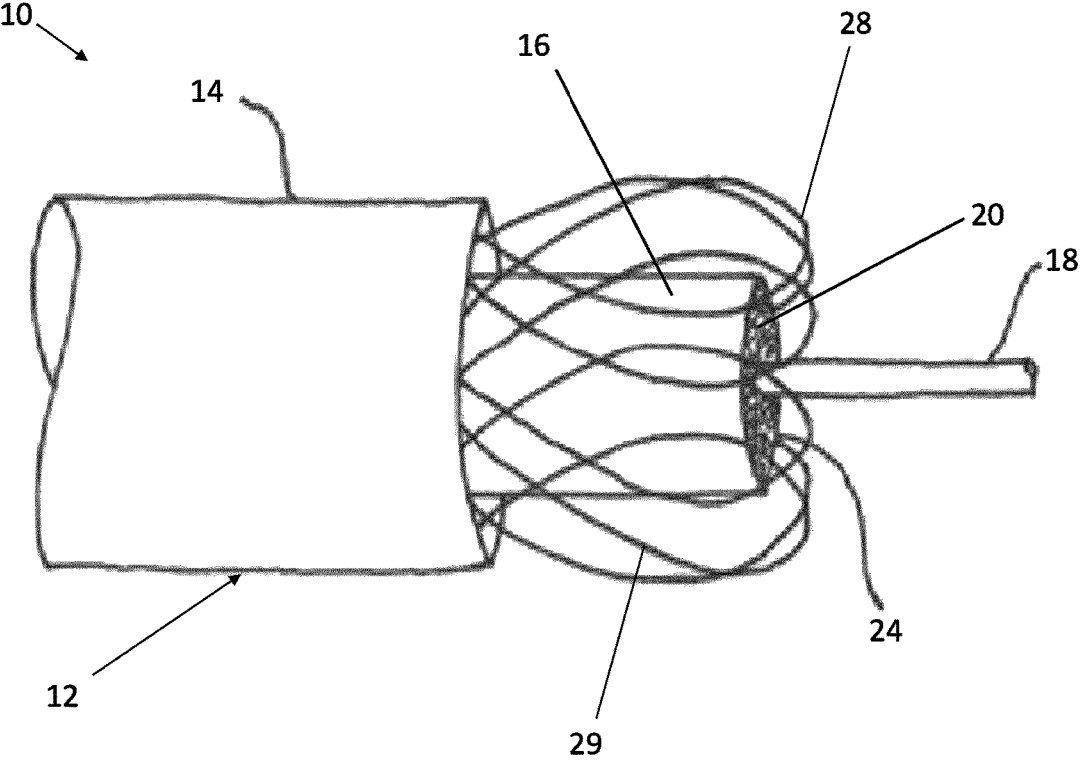

FIG. 2 shows a more detailed example of the device 10 in which the physical barrier comprises a cage 24 that surrounds the cutter 20. The cage 24 can be made from metal strands 26 braided together. The metal strands 26 can be made from any suitable material, such as nitinol, a chromium-cobalt (Cr—Co) alloy, a stainless steel (SST) alloy, and so forth. The cage 24 has a diameter that is slightly larger than a diameter of the cutter 20 (i.e., so that the cage 24 surrounds the cutter 20). For example, the cage 24 can have a diameter of 0.9 mm or larger than the diameter of the cutter 20. To accomplish this, the cage 24 can optionally have a conical or flared shape, as shown in FIG. 2. In another example, shown in FIG. 3, the cage 24 can comprise one or more (unbraided) loops 29 made from metal strands 28, which again may be nitinol, Cr—Co, or other metal or metal alloy strands.

In use, when the catheter 12 is being deployed within the vessel, the physical barrier 22 (e.g., in the form of a balloon or cage) is in a delivery configuration in which the physical barrier 22 is drawn into the outer sheath 14 in a collapsed state (e.g., a deflated balloon or a cage compressed into the outer sheath 14). Once the catheter 12 is positioned within the vessel, the physical barrier 22 is transitioned into an operational configuration, in which the physical barrier is extended outside of the outer sheath 14 in an expanded state. This may entail using a mechanical deployment mechanism such as that used for stent deployment to push the cage 24 out of the outer sheath 14 (or, alternatively, to pull the outer sheath 14 back to release the cage 24) or may entail inflating a balloon serving as the physical barrier 22 using a fluid line extending along the catheter 12.

Figure 4:
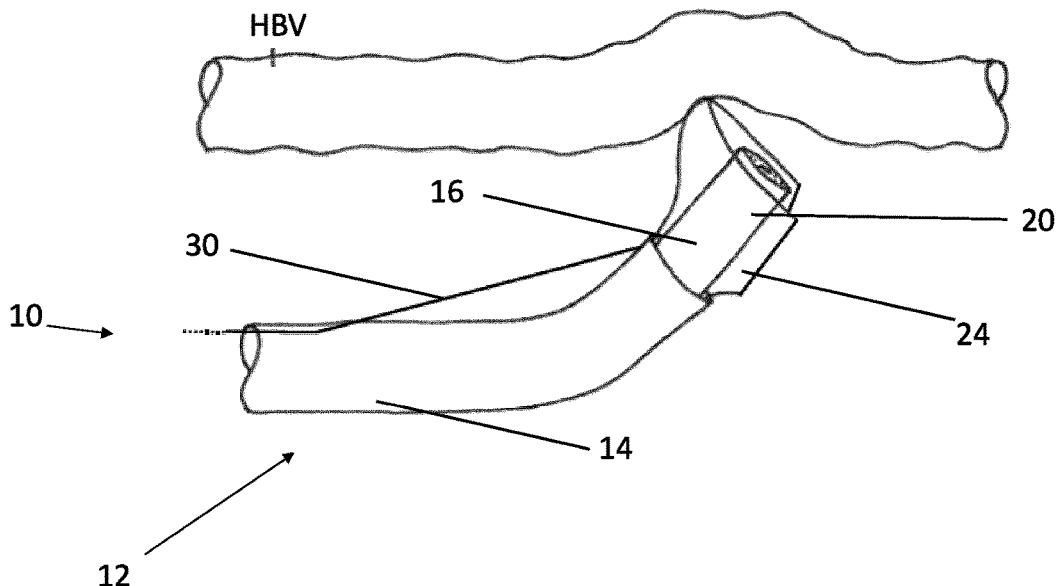

FIG. 4 shows another embodiment of the device 10. As shown in FIG. 4, the device 10 includes a pull wire 30 configured to bend the end of the catheter 12 toward a blood vessel wall. In this case, there is a directionality to the cutting—that is, the cutter 20 will only cut on the side to which the end is bent. Hence, in this case the physical barrier 22 does not need to fully surround the cutter 20 but rather as illustrated is only disposed proximate to the cutter 20, specifically on the side to which the end is bent. FIG. 4 also illustrates that in the case of healthy blood vessel wall HBV, the physical barrier 22 has sufficient stiffness to deflect the healthy blood vessel wall HBV so that the cutter 20 cannot engage and cut the healthy blood vessel wall HBV. This protects the healthy blood vessel wall HBV from inadvertent cutting or perforation.

Figure 5:
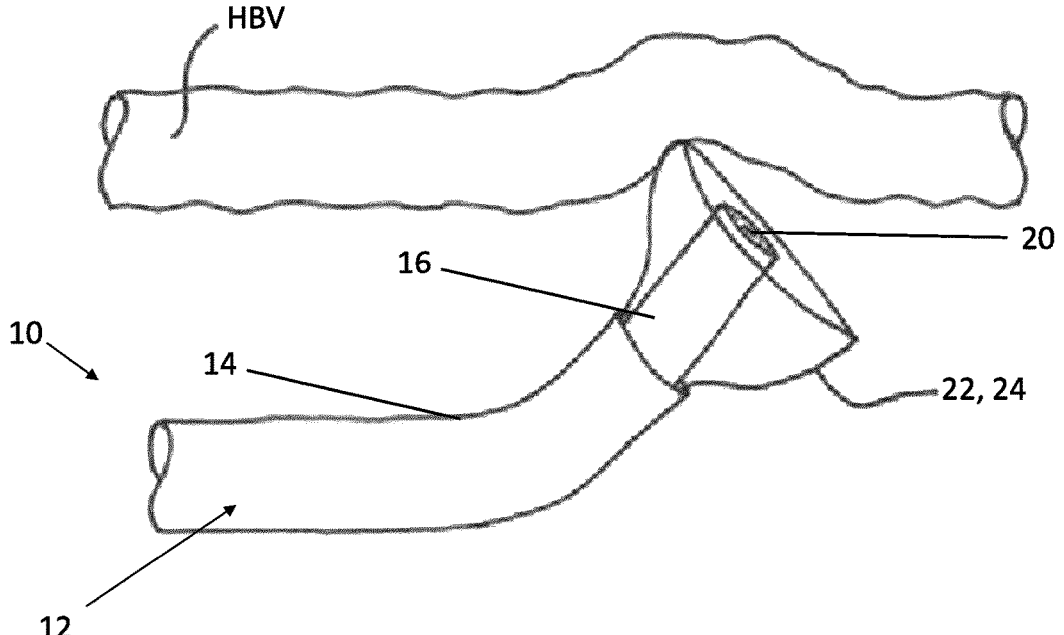
FIGS. 5 and 6 diagrammatically illustrate the device of FIG. 1 in use.
Figure 6:
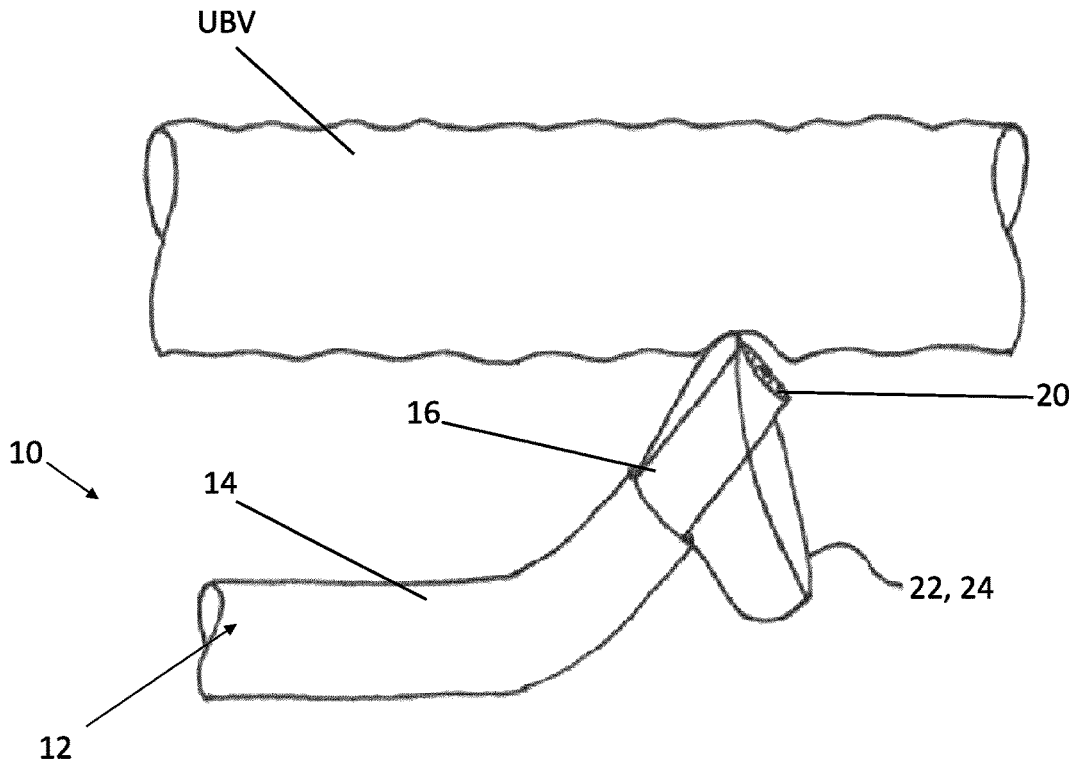

FIGS. 5 and 6 show examples of the device 10 in use. The physical barrier 22 (implemented either has the balloon or the cage 24) has a stiffness effective for the physical barrier 22 to deflect a blood vessel having a thickness less than a first predetermined thickness threshold and effective for a thrombus or atheroma on an inner wall of the blood vessel to deflect the physical barrier. The first predetermined thickness threshold can be, for example, 0.4 mm, which is a typical diameter of a wall of a healthy blood vessel. If the blood vessel has a thrombus or plaque, then the thickness of the blood vessel wall (including the thrombus or plaque) will increase. Furthermore, the material of the thrombus or plaque is usually stiffer than the healthy blood vessel wall.

FIG. 5 shows the device 10 interacting with a healthy blood vessel wall HBV. As shown in FIG. 5, the physical barrier 22, 24 is contacting a wall of the healthy blood vessel HBV having a thickness of (for example) 0.4 mm or less. In this case, the stiffness profile of the physical barrier 22, 24 is sufficient to allow the physical barrier to deflect the wall of the healthy blood vessel HBV away from a potential thrombus or plaque, in which case the blood vessel wall would not be damaged during operation of the cutter 20 on the thrombus or plaque.

On the other hand, FIG. 6 shows the device 10 interacting with an unhealthy blood vessel wall UBV which has a deposit such as a thrombus or atheroma coating its inner surface. This deposit effectively increases the thickness of the unhealthy blood vessel wall UBV, and moreover the material of the deposit typically has higher stiffness than the material of a healthy blood vessel wall. As shown in FIG. 6, the physical barrier 22, 24 is contacting a wall of the unhealthy blood vessel UBV having a thickness of (for example) greater than 0.4 mm. In this case, the stiffness profile of the physical barrier 22, 24 is not sufficient to allow the physical barrier to deflect the wall of the unhealthy blood vessel UBV away from a potential thrombus or plaque. Instead, as seen in FIG. 6, the thrombus or atheroma on the inner wall of the unhealthy blood vessel UBV deflects the physical barrier the physical barrier 22, 24, thereby allowing the cutter 20 to engage (e.g., contact in the case of a physical cutter, or come within the working distance of a laser cutter which is typically around 50 microns) and cut away the thrombus or atheroma.

Figure 7:
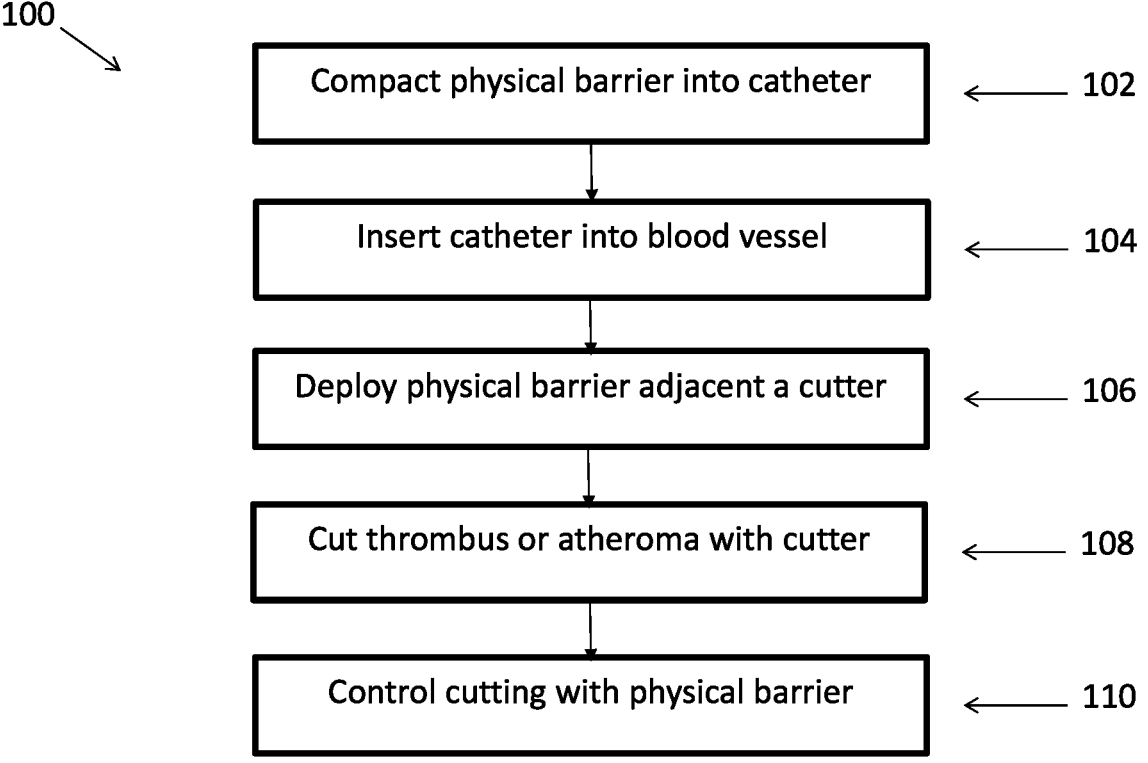
FIG. 7 diagrammatically illustrates a method of performing a thrombectomy and atherectomy using one of the devices of FIG. 1-4.

FIG. 7 shows an example of a flowchart showing a thrombectomy or atherectomy method 100 using the device 10. At an operation 102, the physical barrier 22, 24 is compacted by withdrawing the physical barrier into the outer sheath 14 of the catheter 12. Depending on the deployment mechanism, this can be done by pulling the physical barrier 22, 24 into the outer sheath 14, or by moving the outer sheath 14 forward over the physical barrier 22, 24. In the case of the physical barrier being an inflatable balloon, the compacting operation 102 entails deflating the balloon (or simply installing the balloon in its deflated state). At an operation 104, the catheter 12 is inserted into a blood vessel to deliver the cutter 20 to a thrombus or atheroma disposed on an inner wall of the blood vessel. This may involve initially inserting the guide wire 18 into the blood vessel, and then inserting the catheter 12 along the guide wire 18. In some embodiments, when the physical barrier constitutes the balloon 22, the inserting operation 104 includes maintaining the inflatable balloon in its deflated state. In some embodiments, when the physical barrier constitutes the cage 24, the inserting operation 104 includes maintaining the cage in its collapsed state, i.e., compacted in the outer sheath 14.

At an operation 106, the physical barrier 22, 24 is deployed by extending the physical barrier outside of the outer sheath 14. In some examples, when the physical barrier constitutes the balloon 22, the deploying operation 106 includes inflating the balloon. In other examples, when the physical barrier constitutes the cage 24, the deploying operation 106 includes extending the cage 24 outside of the outer sheath 14 whereby the self-expanding cage (e.g., a cage made of nitinol) expands when extended outside the outer sheath 14. Once deployed, the physical barrier 22, 24 is disposed proximate to the cutter 20.

At an operation 108, the thrombus or atheroma is cut using the cutter 20 to remove at least a portion of the thrombus or atheroma. At an operation 110 (which can be performed during the cutting operation 108), the cutting with the cutter 20 is automatically controlled by way of the physical barrier 22, 24. The physical barrier 22, 24 is deflected by the relatively stiff thrombus or atheroma when cutting the thrombus or atheroma to allow the cutter 20 to engage the thrombus or atheroma; whereas the physical barrier deflects the wall of the blood vessel to prevent the cutter from engaging the wall of the blood vessel. When the material removal is complete, the physical barrier 22 is collapsed (e.g., the balloon is deflated, or the cage is drawn back into the outer sheath 14) and the catheter 12 is withdrawn from the blood vessel (these steps not shown).

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A thrombectomy or atherectomy device, comprising:
a thrombectomy or atherectomy catheter including a cutter; and
a physical barrier disposed proximate to the cutter;
wherein the physical barrier comprises braided metal strands and is configured to control the thrombectomy or atherectomy by being deflected during the thrombectomy or atherectomy and deflecting a wall of a blood vessel to prevent the cutter from engaging the wall of the blood vessel and wherein the physical barrier comprises a cage surrounding the cutter, the cage having a diameter that is at least 0.9 millimeters larger than a diameter of the cutter.

2. The device of claim 1, wherein the physical barrier has a stiffness effective for the physical barrier to deflect a blood vessel having a thickness less than a first predetermined thickness threshold and effective for a thrombus or atheroma on an inner wall of the blood vessel to deflect the physical barrier.

3. The device of claim 2, wherein the first predetermined thickness blood vessel is 0.4 mm.

4. The device of claim 1, wherein the cutter comprises a rotating cutter, an abrasion cutter, or a laser cutter.

5. The device of claim 1, further comprising at least one sheath configured to move along a guide wire.

6. The device of claim 1, wherein the cage has a conical or flared shape.

7. The device of claim 1, wherein the physical barrier comprises nitinol.

8. The device of claim 1, wherein the physical barrier is comprised of a chromium-cobalt (Cr—Co) alloy or a stainless steel (SST) alloy.

9. The device of claim 1, further comprising an inner sheath on which the cutter is disposed and an outer sheath surrounding the inner sheath, wherein:
the physical barrier is drawn into the outer sheath in a delivery configuration; and
the physical barrier is extended outside the outer sheath in an operational configuration.

10. A thrombectomy or atherectomy device, comprising:
a thrombectomy or atherectomy catheter including a cutter; and
a physical barrier disposed proximate to the cutter;
wherein the physical barrier comprises braided metal strands and is configured to control the thrombectomy or atherectomy by being deflected during the thrombectomy or atherectomy and deflecting a wall of a blood vessel to prevent the cutter from engaging the wall of the blood vessel, and wherein the physical barrier comprises a cage surrounding the cutter, wherein the cage comprises braided strands of nitinol.

11. A thrombectomy or atherectomy device, comprising:
a thrombectomy or atherectomy catheter including a cutter; and
a cage disposed proximate to the cutter, the cage comprising braided metal strands and having a stiffness effective for the cage to deflect a blood vessel having a thickness less than a first predetermined thickness threshold and effective for a thrombus or atheroma on an inner wall of the blood vessel to deflect the cage and configured to control the thrombectomy or atherectomy by being deflected during the thrombectomy or atherectomy and deflecting a wall of a blood vessel to prevent the cutter from engaging the wall of the blood vessel.

12. The device of claim 11, wherein the cage has a diameter that is at least 0.9 millimeters larger than a diameter of the cutter.

13. A thrombectomy or atherectomy method comprising:
inserting a catheter carrying a cutter into a blood vessel to deliver the cutter to a thrombus or atheroma disposed on an inner wall of the blood vessel;
cutting the thrombus or atheroma using the cutter to remove at least a portion of the thrombus or atheroma; and
controlling the cutting using a physical barrier disposed proximate to the cutter, the physical barrier being deflected when cutting the thrombus or atheroma to allow the cutter to engage the thrombus or atheroma and the physical barrier deflecting the wall of the blood vessel to prevent the cutter from engaging the wall of the blood vessel.

14. The method of claim 13, further comprising:
prior to the inserting, compacting the physical barrier by withdrawing the physical barrier into an outer sheath of a catheter carrying the cutter; and
after the inserting and before the cutting, deploying the physical barrier by extending the physical barrier outside of the outer sheath whereby the physical barrier is disposed proximate to the cutter.

15. The method of claim 13, wherein the physical barrier comprises an inflatable balloon, and the method further comprises:
during the inserting, maintaining the inflatable balloon in a deflated state; and
after the inserting and before the cutting, inflating the balloon whereby the inflated balloon is disposed proximate to the cutter.

16. The method of claim 13, wherein the physical barrier comprises a cage, and the method further comprises:
during the inserting, maintaining the cage in a collapsed state; and
after the inserting and before the cutting, deploying the cage into an expanded state.

* * * * *